United States Patent [19]
Fukami

[11] Patent Number: 5,509,422
[45] Date of Patent: Apr. 23, 1996

[54] CLINICAL THERMOMETER WITH PULSIMETER

[76] Inventor: Tetsuji Fukami, 9-33, 3-chome, Kotabe, Sawara-ku, Fukuoka-shi, Fukuoka-ken, Japan

[21] Appl. No.: 321,970

[22] Filed: Oct. 12, 1994

[30] Foreign Application Priority Data

Apr. 14, 1994 [JP] Japan .................................. 6-075946
May 9, 1994 [JP] Japan .................................. 6-095197

[51] Int. Cl.$^6$ .................................................. A61B 5/0205
[52] U.S. Cl. ......................................... 128/670; 128/736
[58] Field of Search .................................. 128/670, 736, 128/696

[56] References Cited

U.S. PATENT DOCUMENTS

| | | | |
|---|---|---|---|
| 3,916,877 | 11/1975 | Beckman | 128/670 |
| 3,999,537 | 12/1976 | Noiles | 128/736 |
| 4,312,358 | 1/1982 | Barney | 128/670 |
| 4,686,998 | 8/1987 | Robbins | 128/670 |
| 4,825,874 | 5/1989 | Uhlemann | 128/896 |
| 4,844,090 | 7/1989 | Sekine | 128/696 |

FOREIGN PATENT DOCUMENTS

| | | | |
|---|---|---|---|
| 3613889 | 10/1987 | Germany | 128/670 |
| 8805282 | 7/1988 | WIPO | 128/736 |

*Primary Examiner*—Angela D. Sykes
*Assistant Examiner*—Eric F. Winakur
*Attorney, Agent, or Firm*—Brooks Haidt Haffner & Delahunty

[57] ABSTRACT

A clinical thermometer equipped with a pulsimeter particularly for measuring a body temperature and a pulse rate at the same time. Such a thermometer has first and second electric conductors. A temperature sensor is arranged on the second electric conductor via a heat insulator or directly arranged without such an insulator. With such a construction, the temperature sensor measures a body temperature, while the first and second electric conductors measure a pulse rate and electrocardiographic variation.

6 Claims, 4 Drawing Sheets

FIG. 3
FIG. 4
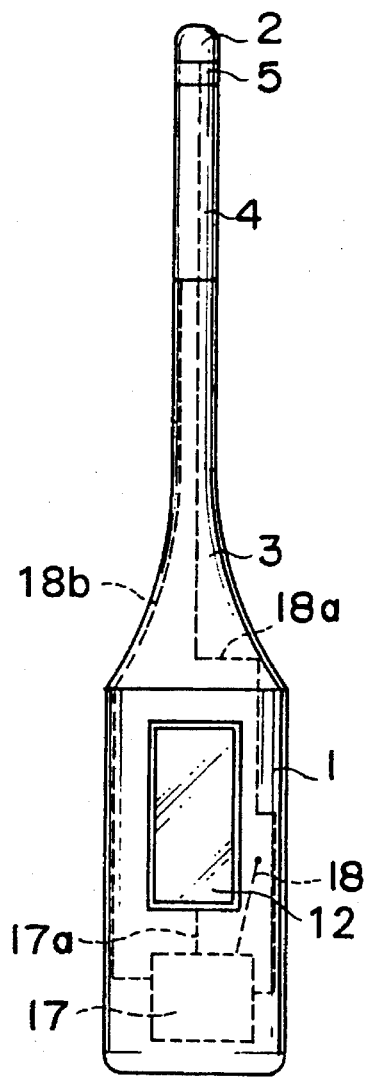
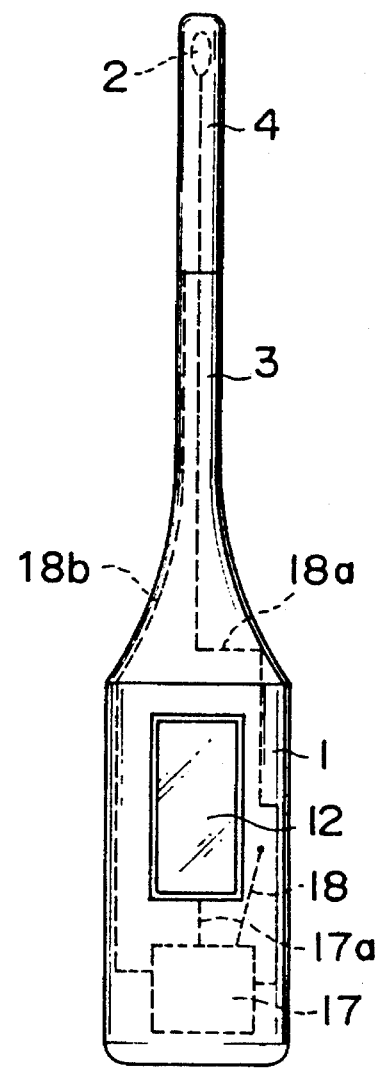

CLINICAL THERMOMETER WITH PULSIMETER

BACKGROUND OF THE INVENTION

1. Field of the Invention

The present invention relates to a clinical thermometer equipped with a pulsimeter, and more particularly, to a novel improvement for measuring a body temperature and a pulse rate at the same time.

2. Description of the Related Art

Conventionally, a method of measuring a body temperature and a pulse rate is employed whereby a body temperature is measured by a mercury thermometer or an electronic thermometer, and then, a pulse rate is manually measured by a doctor or a nurse, or by an automatic sphygmomanometer. That is, a clinical thermometer and a pulsimeter are independently used.

Since such a conventional measurement method is employed as described above, it presents the following problems.

That is, a body temperature and a pulse rate are separately measured in the foregoing method, which is time-consuming and troublesome, thus hampering a speedy treatment.

SUMMARY OF THE INVENTION

Accordingly, in order to overcome the above drawbacks, an object of the present invention is to provide a clinical thermometer equipped with a pulsimeter in which an improvement has been made by measuring a body temperature and a pulse rate at the same time..

In order to achieve the above objects, according to one aspect of the present invention, there is provided a clinical thermometer equipped with a pulsimeter, comprising: a first electric conductor provided with a temperature sensor at the forward end, the temperature sensor measuring a body temperature; and a second electric conductor formed of an electric conducting material so as to be connected to the first electric conductor via an insulator, the first and second electric conductors measuring a pulse rate.

More specifically, such a clinical thermometer may further comprise a first pulse lead wire provided for the first electric conductor and a second pulse lead wire provided for the second electric conductor.

Further, first and second temperature sensor lead wires of the temperature sensor and the first and second pulse lead wires are introduced to the exterior from the second electric conductor used as a handle.

According to another aspect of the present invention, there is provided a clinical thermometer equipped with a pulsimeter, comprising: a first electric conductor; a second electric conductor connected to the first electric conductor via an insulator, the first and second electric conductors measuring a pulse rate; and a temperature sensor connected to the second electric conductor via a heat insulator so as to measure a body temperature.

According to still another aspect of the present invention, there is provided a clinical thermometer equipped with a pulsimeter, comprising: a first electric conductor; a second electric conductor connected to the first electric conductor via an insulator, the first and second electric conductors measuring a pulse rate; and a temperature sensor built into the second electric conductor so as to measure a body temperature.

The first electric conductor may be provided with an indicator for indicating a body temperature and a pulse rate.

According to a further aspect of the present invention, there is provided a clinical thermometer equipped with a pulsimeter, comprising: a first electric conductor exposed from a main body; a second electric conductor connected to the main body via a signal line, the first and second electric conductors measuring a pulse rate; and a temperature sensor connected to the second electric conductor via a heat insulator so as to measure a body temperature.

According to an even further aspect of the present invention, there is provided a clinical thermometer equipped with a pulsimeter, comprising: a first electric conductor exposed from a main body; a second electric conductor connected to the main body via a signal line, the first and second electric conductors measuring a pulse rate; and a temperature sensor built into the second electric conductor so as to measure a body temperature.

The main body may be provided with an indicator for indicating a body temperature and a pulse rate.

According to the clinical thermometer equipped with a pulsimeter of the present invention, such a probe is brought into contact with a predetermined region of a testee so as to allow a body temperature signal obtained in the temperature sensor to be sent out to the exterior from the temperature sensor lead wires, and simultaneously to permit a pulse signal obtained across the first and second electric conductors to be sent out to the exterior. Hence, the testee simply touches the single probe so that he/she is able to simultaneously fetch two pieces of data, such as a body temperature and a pulse rate, thus considerably saving the time and effort of whoever does the measurement, the testee or a nurse.

BRIEF DESCRIPTION OF THE DRAWINGS

FIG. 3 is a schematic view of a thermometer with a pulsimeter according to a second embodiment of the present invention;

FIG. 4 is a schematic view of a modification of the thermometer shown in FIG. 3;

DESCRIPTION OF THE PREFERRED EMBODIMENTS

Figure 1:
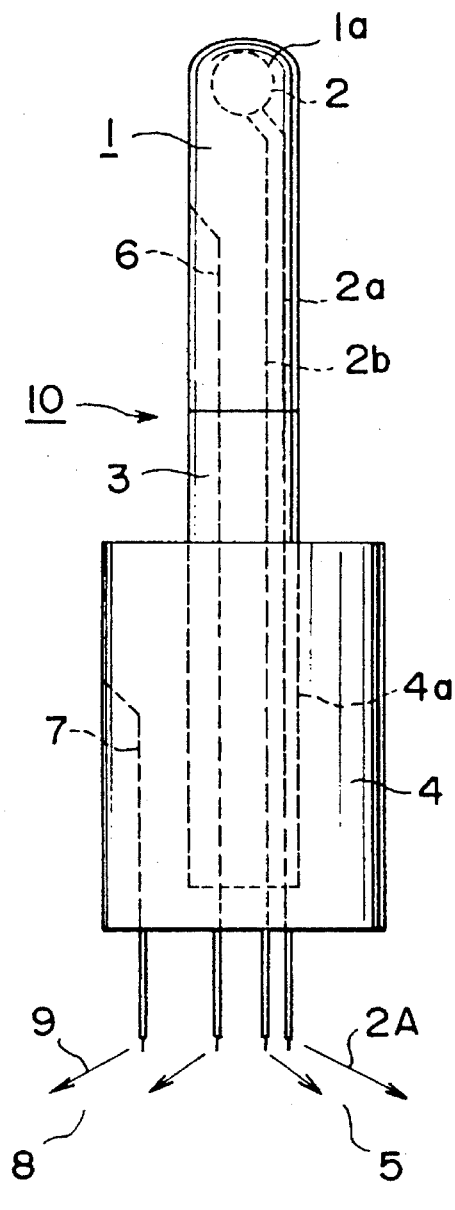
FIG. 1 is a schematic view of a clinical thermometer equipped with a pulsimeter according to a first embodiment of the present invention.
Figure 2:
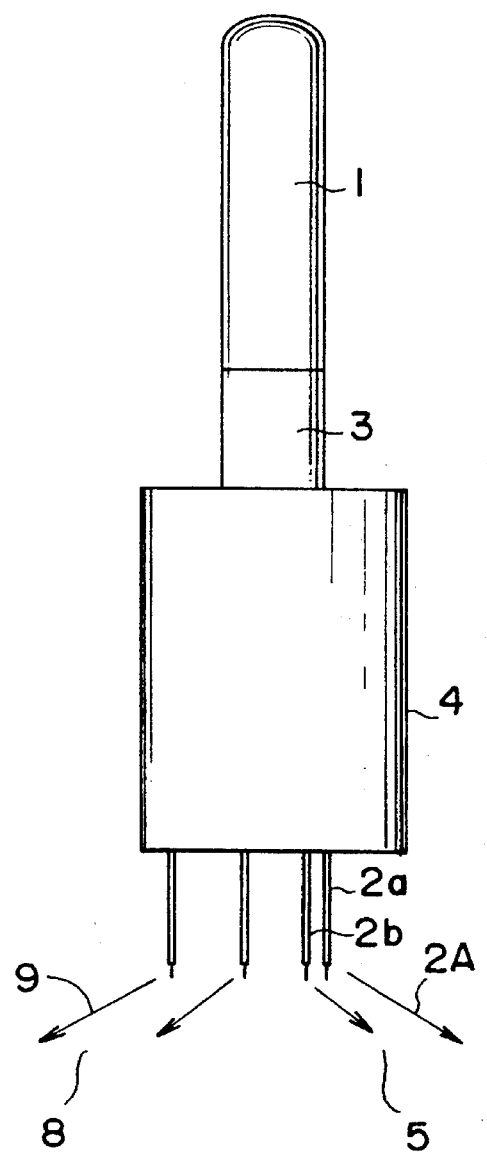
FIG. 2 is an outer view of the thermometer shown in FIG. 1.

A detailed description will now be given of preferred embodiments of a probe for measuring a body temperature and electrocardiographic variation according to the present invention with reference to the drawings, A probe generally denoted by 10 of a first embodiment is shown in FIGS. 1 and 2. A bar-like first electric conductor 1 is formed of an electric conducting material and has a temperature sensor 2 at the forward end 1a. A second electric conductor 4 is formed of an electric conducting material and constitutes a handle. The first electric conductor 1 is fittingly connected to the second electric conductor 4 via an insulator 3 by use of a hole 4a, thereby integrally forming the electric conductors 1 and 4.

First and second temperature sensor lead wires 2a, 2b connected to the temperature sensor 2 are constructed to allow a body temperature signal 2A to be transmitted to a temperature measurement circuit 5. That is, such wires 2a and 2b pass through the first electric conductor 7, the insulator 3 and the second electric conductor 4 so as to be introduced to the exterior from the second electric conductor 4.

First and second pulse lead wires 6 and 7 are constructed to permit a pulse signal 9 to be transmitted to a pulse detection circuit 8. That is, the first pulse lead wire 6 provided for the first electric conductor 1 passes through the first electric conductor 1, the insulator 3 and the second electric conductor 4 so as to be introduced to the exterior from the second electric conductor 4, while the second pulse lead wire 7 provided for the second electric conductor 4 is introduced to the exterior from such a second electric conductor 4. The first and second electric conductors 1 and 4 thus form a pulse sensor.

The operation of the probe constructed as described above will now be described. A testee (not shown) first holds the second electric conductor 4 used as a handle of the probe 10 with a hand and brings the first electric conductor 1 into a contact with a predetermined region of the body. Then, the body temperature signal 2A obtained in the temperature sensor 2 is sent out to the exterior through the first and second temperature sensor lead wires 2a and 2b so as to be transmitted to the temperature measurement circuit 5. Meanwhile, the pulse signal 9 obtained across the first and second electric conductors 1 and 4 is concurrently transmitted to the pulse detection circuit 8. In this manner, the testee is able to measure both body temperature and electrocardiographic variation with the single probe The respective components of the foregoing embodiment are illustrated only, and various modifications of such components, such as the shape, or the like, may be made, in which case, advantages similar to those in the above embodiment can be obtained.

An explanation will now be given of other embodiments illustrated in FIGS. 3–6. Components corresponding to those in FIGS. 1 and 2 have been given the same reference numerals as in FIGS. 1 and 2.

FIG. 3 illustrates a second embodiment in which a first electric conductor 1 is provided with an indicator for indicating a body temperature and a pulse rate. The first electric conductor 1 is formed of an electric conducting material so that it can be directly conducted when it is brought into contact with any region of the body. Such a conductor 1 also constitutes a handle.

Connected to the first electric conductor 1 through a tapered insulator 3 is a bar-like second electric conductor 4. A temperature sensor 2 is connected to the second electric conductor 4 through a heat insulator 5 formed of a heat insulating material. The first electric conductor 1 has a built-in detection circuit 17 which output 17a is input into the indicator 12.

The first and second electric conductors 1 and 4 are connected to the detection circuit 17 via built-in lead wires 18 and 18b, and a cable 18a containing the wires from temperature sensor 2 is also connected to the detection circuit 17.

With the foregoing construction, the temperature sensor 2 and the second electric conductor 4 are applied to the armpit, while the first electric conductor 1 is held with a hand. The thus obtained temperature signal in the temperature sensor 2 is processed in the detection circuit 17 so as to be indicated on the indicator 12, while an electrocardiographic variation obtained in the electric conductors 1 and 4 is transformed into a pulse as a known potential difference so as to be indicated on the indicator 12 as a pulse rate via the detection circuit 17.

FIG. 4 illustrates a modification of the second embodiment shown in FIG. 3. The second electric conductor 4 having a built-in temperature sensor 2 is arranged on the top of the insulator 3, and other constructions are similar to those shown in FIG. 3. The same components as those shown in FIG. 3 are designated by like reference numerals and an explanation thereof will thus be omitted.

Figure 5:
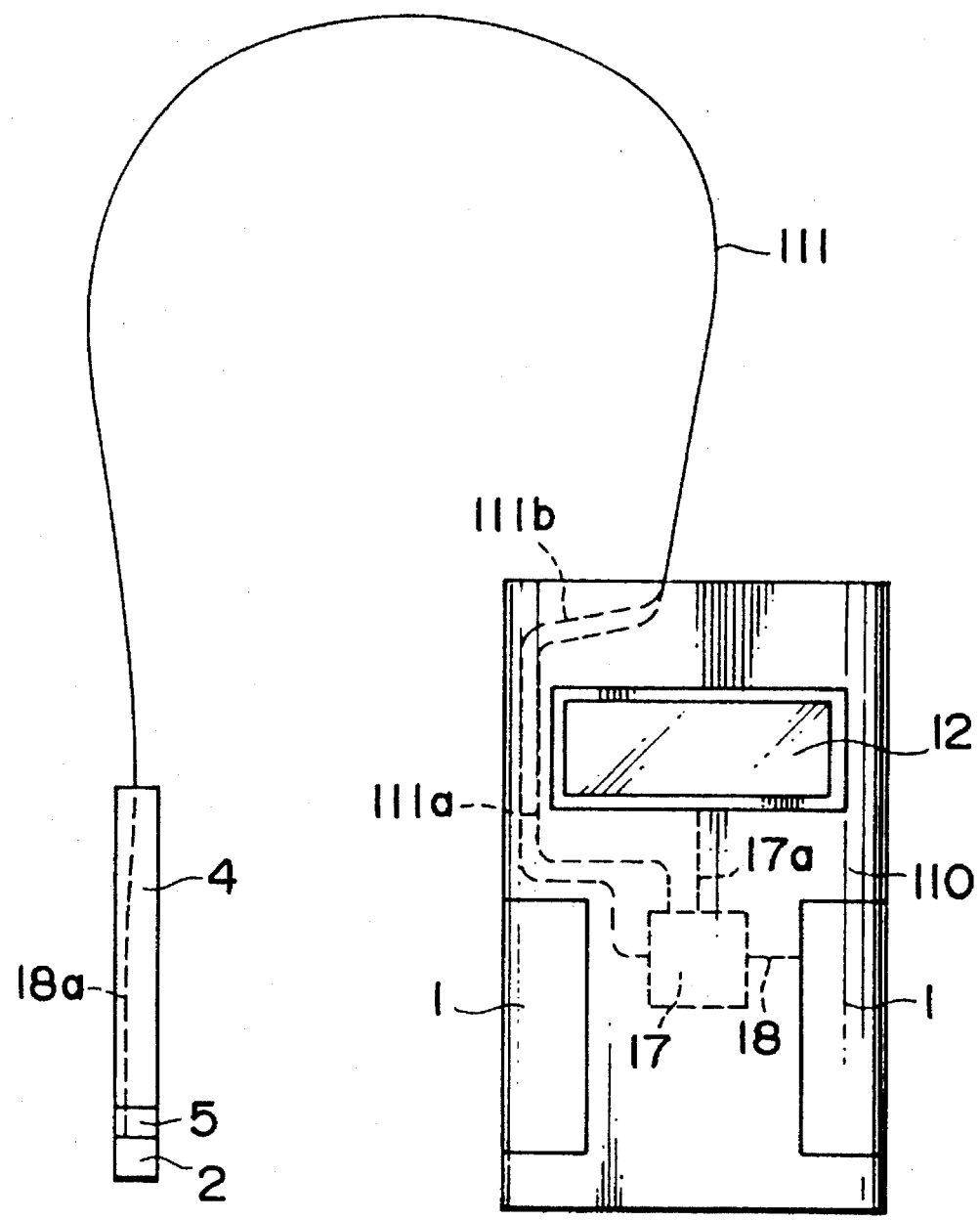
FIG. 5 is a schematic view of a thermometer equipped with a pulsimeter according to a third embodiment of the present invention.

In a third embodiment illustrated in FIG. 5, a main body used as a handle 110 is formed of an insulating material and includes a first electric conductor 1, a detection circuit 17 and an indicator 12 which are all exposed to the external surface of the main body 110. The output 17a of the detection circuit 17 is input into the indicator 12 and the first electric conductor 1 is connected to the detection circuit 17 via a lead wire 18.

Connected to the main body 110 is the second electric conductor 4 via a signal line 111 formed of an external cable. A temperature sensor 2 is arranged on top of the second electric conductor 4 through a heat insulator 5. The temperature sensor 2 is connected to the detection circuit 17 via a cable 18a, the signal line 111 and a wire pair 111a, while the second electric conductor 4 is connected to the detection circuit 17 via the signal line 111 and a lead wire 111b.

According to the construction as described above shown in FIG. 5, the main body 110 is held with a hand and the first electric conductor 1 is touched. While remaining such a state, the temperature sensor 2 and the second electric conductor 4 are applied to the armpit so as to allow the body temperature measured in the temperature sensor 2 to be processed in the detection circuit 17 and to be indicated on the indictor 12 in a manner similar to the foregoing embodiments. The pulse rate generated across the electric conductors 1 and 4 along with the electrocardiographic operation is also processed in the detection circuit 17 so as to be indicated on the indicator 12.

Figure 6:
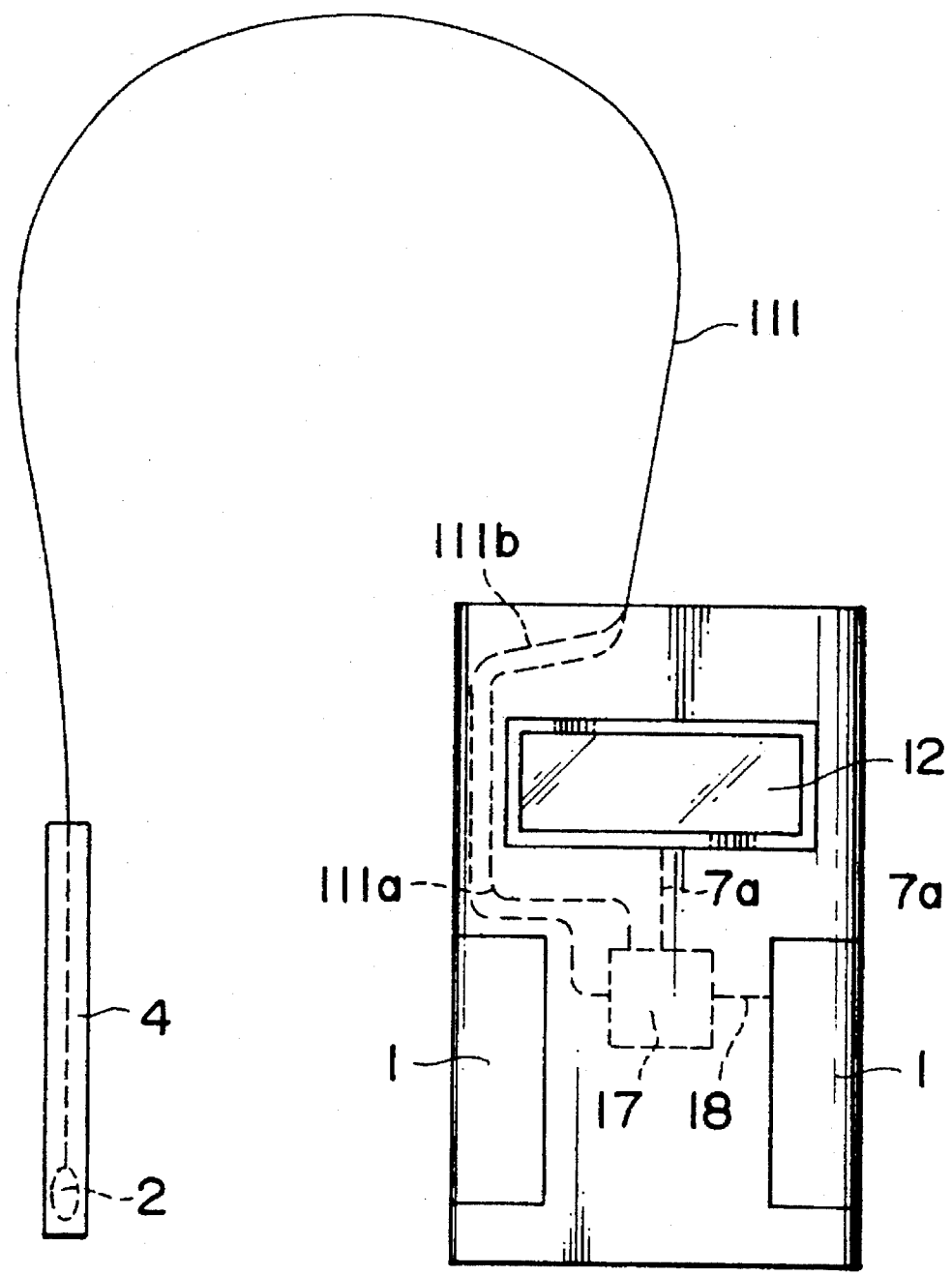
FIG. 6 is a schematic view of a modification of the third embodiment shown in FIG. 5.

FIG. 6 illustrates a modification of the embodiment shown in FIG. 5. Such a modification is constructed such that a temperature sensor 2 is built within the second electric conductor 4, and the other components are similar to those shown in FIG. 5. The same components as those shown in FIG. 5 are designated by like reference numerals and an explanation thereof will thus be omitted.

As will be clearly understood from the foregoing description, the present invention offers the following advantages.

The clinical thermometer equipped with a pulsimeter according to the present invention is constructed such that a temperature sensor for measuring a body temperature is integrally formed with a pair of electric conductors for measuring a pulse rate. The body temperature and the pulse rate can thus be measured at the same time, thus considerably shortening the time required for such measurements during a medical examination, thereby enhancing efficient examination which is significantly shortened by the present invention.

What is claimed is:

1. A clinical thermometer in combination with a pulsimeter comprising:

a first hollow cylinder having a closed end, and an open end and formed of an electrically and thermally conductive material, said first cylinder having a first diameter, a second hollow cylinder formed of an electrically conductive material and having a diameter larger than said first diameter and suitable to be hand held, a cylindrical body of electrically nonconductive and thermally insulative material joining said first cylinder at said open end substantially coaxially to a first end of said second cylinder, a thermoelectric transducer disposed within said first hollow cylinder adjacent said closed end thereof for sensing temperature transmitted through said first cylinder, and a plurality of electric conductors disposed within said hollow cylinders and said cylindrical body, wherein two of said electric conductors are connected to said transducer for connecting said transducer to means for measuring the temperature to which said transducer is exposed, and two more of said electric conductors are connected to said hollow cylinders, one to each, for connecting said hollow cylinders to means for measuring pulse rate.

2. A clinical thermometer in combination with a pulsimeter according to claim 1, in which said means for measuring the temperature and said means for measuring pulse rate are disposed within said second hollow cylinder.

3. A clinical thermometer in combination with a pulsimeter according to claim 2, wherein said second cylinder has a window formed therein, and said means for measuring the temperature and said means for measuring pulse rate include a display element visible through said window.

4. A clinical thermometer in combination with a pulsimeter comprising:

a cylindrical body having a first section at one end with a diameter suitable to be hand held, an intermediate tapered section, and at the other end of said cylindrical body a narrow section with a closed distal end of smaller diameter than said first section, said intermediate section providing a transition between said first section and said narrow section, a first hollow cylinder formed of an electrically conductive material surrounding said narrow section near but spaced from the closed distal end of said narrow section, a second hollow cylinder formed of an electrically conductive material surrounding said first section, a thermoelectric transducer disposed at said closed distal end of said narrow section spaced from and thermally isolated from said first hollow cylinder, and a plurality of electric conductors disposed within said cylindrical body, wherein two of said electric conductors are connected to said transducer for connecting said transducer to means for measuring the temperature to which said transducer is exposed, and two more of said electric conductors are connected to said hollow cylinders, one to each, for connecting said hollow cylinders to means for measuring pulse rate.

5. A clinical thermometer in combination with a pulsimeter according to claim 4, in which said means for measuring the temperature and said means for measuring pulse rate are disposed within said first section of said cylindrical body.

6. A clinical thermometer in combination with a pulsimeter according to claim 5, wherein said first section has a window formed therein, and said means for measuring the temperature and said means for measuring pulse rate include a display element visible through said window.

* * * * *